United States Patent [19]

Zimmerman

[11] Patent Number: 5,029,358
[45] Date of Patent: Jul. 9, 1991

[54] INTERPROXIMAL BRUSH

[75] Inventor: Walter Zimmerman, Atherton, Calif.

[73] Assignee: The Gillette Company, Boston, Mass.

[21] Appl. No.: 463,105

[22] Filed: Jan. 10, 1990

[51] Int. Cl.[5] .............................. A46B 3/08; A46B 3/18
[52] U.S. Cl. ..................................... 15/167.1; 15/145;
15/206; 15/106; 15/110
[58] Field of Search ...................... 15/106, 167.1, 110

[56] References Cited

U.S. PATENT DOCUMENTS

| 4,030,199 | 6/1977 | Russell | 15/106 |
| 4,319,377 | 3/1982 | Tarrson et al. | 15/167.1 |
| 4,387,479 | 6/1983 | Kigyos | 15/167.1 |
| 4,691,404 | 9/1987 | Tarrson et al. | 15/167.1 |
| 4,751,761 | 6/1988 | Breitschmid | 15/167.1 |
| 4,780,923 | 11/1988 | Schultheiss | 15/167.1 |

Primary Examiner—Harvey C. Hornsby
Assistant Examiner—Patrick F. Brinson
Attorney, Agent, or Firm—John P. Morley; Aubrey C. Brine

[57] ABSTRACT

An interproximal brush comprises a handle having an end portion provided with a transverse hole communicating with a longitudinal groove for receiving the elongated stem of an interproximal brush. The handle further has a cylindrical boss formed on the lower surface thereof through which the transverse hole extends, and the brush stem is retained securely in the longitudinal groove on closure of a cap, which is pivotably attached to the end portion.

8 Claims, 1 Drawing Sheet

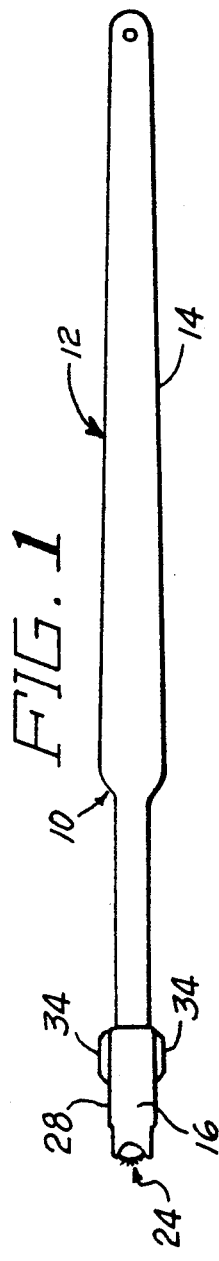
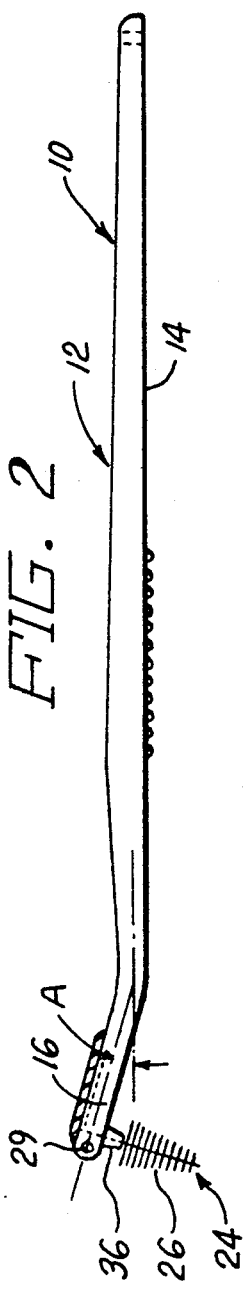
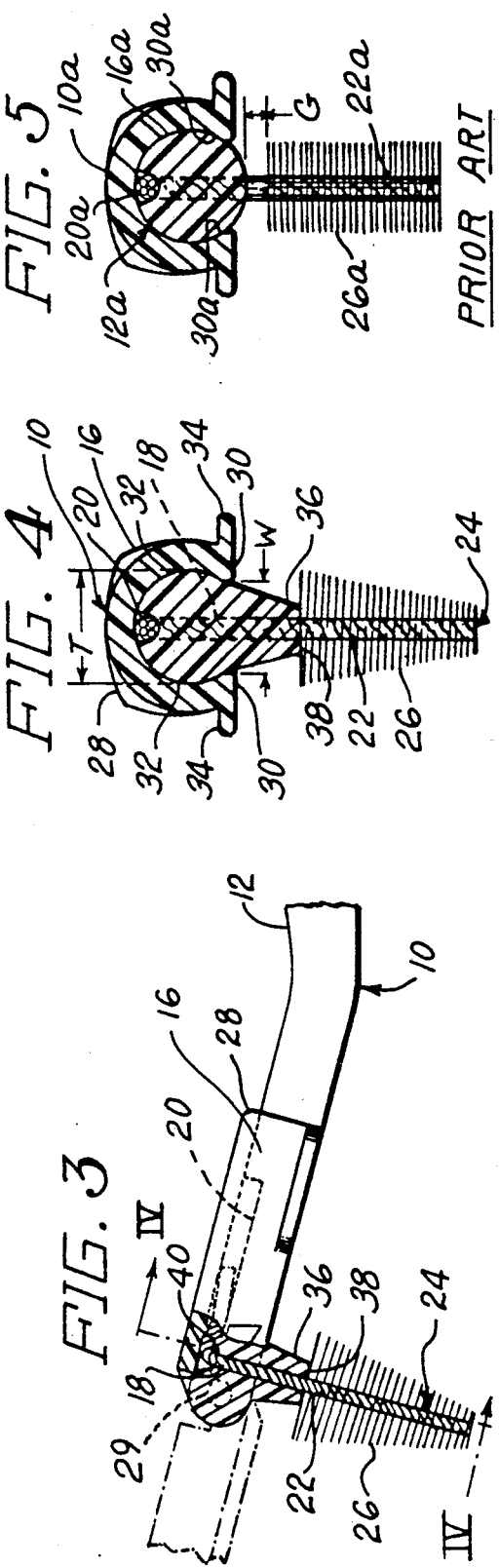

INTERPROXIMAL BRUSH

BACKGROUND OF THE INVENTION

The present invention relates to interproximal brush devices for oral care and more particularly to a brush of the type in which a disposable brush element is retained on a handle by a removable cap member.

A great number of devices exist in the prior art which have been developed for performing the cleaning of teeth and massaging of the gums. The brushes generally have bristles which rub or wipe perpendicularly across the gum and tooth surfaces, and one type of disposable brush has twisted wire bristles which are captured between, and extend radially from, a pair of twisted metal wires. One such brush is disclosed in U.S. Pat. No. 4,780,923 issued to Peter Schultheiss on Nov. 1, 1988 and assigned to the assignee of the present invention.

Other brushes which have been employed for similar usage are found in U.S. Pat. No. 4,222,143 to Tarrson et al disclosing an interproximal brush handle utilizing a slidable sleeve to retain a brush, U.S. Pat. No. 4,030,199 to Russel which discloses a handle for holding a stem mounted disposable brush and utilizes a slidable tapered sleeve for retaining the brush in a friction fit, U.S. Pat. No. 3,559,226 to Burns which discloses a toothbrush having a metal handle for holding an interproximal brush with a holding chuck utilizing screw threads, knurling, or the like to retain the brush. Other patents which have been referred to in U.S. Pat. No. 4,780,923 cited above are U.S. Pat. No. 4,296,518 to Furrier et al which discloses a toothbrush with fixed bristles and a gum massaging accessory which is pivotably attached to a handle and U.S. Pat. No. 4,319,377 to Tarrson et al disclosing an interproximal toothbrush which uses a threaded sleeve retainer for the disposable brush.

While the above cited U.S. Pat. No. 4,780,923 discloses a device which has proven to be successful in the marketplace, it is considered that an improvement in the product could be made without a substantial increase in cost to the user, which would provide a product more desirable to some of the users' needs.

It has been found that in the device shown in the aforementioned U.S. Pat. No. 4,780,923 (which is herein incorporated by reference), the users in some instances, when threading the stem of the brush member through a transverse hole in the handle, were leaving a gap of as much as one-quarter inch between the handle and the bristles of the brush. This leads to bending of the brush and in frequent instances would cause breaking of the brush stem adjacent the handle.

It is also found that the clear color of the plastic employed in manufacturing the handle did not provide a distinct view of the transverse hole to many of the older users, therefore providing difficulty in threading the stem of the brush into the handle.

It is therefore an object of the present invention to provide an interproximal brush, employing disposable brush members, which facilitates the threading of a brush stem into the handle.

It is a further object of the invention to provide an interproximal brush of the type described wherein the brush stem is given additional support against breakage of the brush during use.

SUMMARY OF THE INVENTION

The aforementioned objects, and other objectives which will become apparent as the description proceeds, are accomplished by providing an interproximal brush employing a disposable brush member which comprises an elongated handle having a disposable brush at one end thereof and a grip portion at the opposite end. The brush retaining means generally comprises opposed side surfaces and a bottom surface of the one handle end, a transverse hole formed in the handle and a longitudinal groove arranged for communication with the transverse hole. The bottom surface has a downwardly extending boss formed thereon and disposed with the transverse hole extending through the boss substantially at the centerline of the boss. A cap is mounted at the brush retaining end portion which includes a section adopted and arranged for overlying the longitudinal groove and the top end of the transverse hole.

A brush member is provided having a stem which is inserted through the transverse hole extending through the boss and the handle, and is retained in the groove. A radial protuberance may be provided extending laterally across the longitudinal groove adjacent the transverse hole to aid in bending a portion of the stem extending through the transverse hole, into the groove.

The boss is generally in the form of a frustrum, and may be molded as an integral part of the brush retaining means formed on the handle.

BRIEF DESCRIPTION OF THE DRAWING

The foregoing and other features of the invention will be more particularly described in connection with the preferred embodiment, and with reference to the accompanying drawing, wherein:

FIG. 1 is a top plan view showing an interproximal brush constructed in accordance with the teachings of the present invention;

FIG. 2 is a side elevational view partially in section showing details of the interproximal brush of FIG. 1;

FIG. 3 is a fragmentary sectional view showing details of a portion of the interproximal brush of FIGS. 1 and 2, taken on an enlarged scale for clarity;

FIG. 4 is a front sectional view taken along the lines IV—IV of FIG. 3 showing further details of the interproximal brush of FIGS. 1 through 3; and FIG. 5 is a front section view similar to FIG. 4 showing an interproximal brush of the prior art.

DESCRIPTION OF THE PREFERRED EMBODIMENT

Referring now to the drawing and in particular to FIGS. 1 through 4, there is shown an interproximal brush 10 comprising an elongated handle 12 having a grip portion 14 at one end thereof and a brush retaining means formed at the opposite end 16 thereof. The end 16 of the brush handle 12 containing the brush retaining means has a reduced thickness or diameter from that of the grip portion 14 and is bent upwardly at an angle from about 5° to about 25° with respect to the longitudinal axis of the handle 12, as best shown in FIG. 2 of the drawing. A transverse hole 18 extends through the brush retaining end 16 of the handle 12 and is in communication with a longitudinal groove 20 extending rearwardly from the hole 18.

The hole 18 is dimensioned to allow a stem 22 of an interproximal brush 24 to be easily inserted through the transverse hole 18 and to restrain movement of the twisting of the stem to any significant degree when the stem is positioned within the transverse hole. The interproximal brush 24 is similar to that shown in the aforementioned U.S. Pat. No. 4,780,923 and is one of a type well known in the art and generally available through normal trade outlets. The brush 24 is generally manufactured having bristles extending radially from the stem 22, the stem generally comprising a pair of twisted wires. Interproximal brushes of this type can be of the conical shape shown in FIGS. 1 through 4, or of the cylindrical shape shown in FIG. 5. Additionally, the stiffness of the bristles can vary from degrees of softness to degrees of hardness and the bristles may be of natural or synthetic fibers with nylon fibers being preferred. Any of the several different types of interproximal brushes can be used in the handle of the present invention. Further details relating to interproximal brushes can be found in U.S. Pat. No. 4,395,943.

The longitudinal groove 20 is designed to provide a locking groove for capturing and retaining a length of the stem 22 which extends above the handle 12 when inserted into the transverse hole 18. Accordingly, groove 20 is of a dimension wide and deep enough to receive the stem 22 and long enough to receive a fairly precise length of stem, which will insure that the bristle portion 26 projects a predetermined distance beyond the brush retaining end 16 when the stem is bent downwardly and thrust into the groove 20.

A molded polymeric cap 28 is pivotably connected by a pin 29 and disposed to overlie the groove 20 and retain that portion of the stem 22 within the groove, when in the closed position. As best shown in FIG. 4, the cap 28 has opposed side edges 30 which are flexible and are spaced apart by a dimension W. Dimension W is selected so that flexible edges 30 will flex outwardly when at least a portion of the edges engage opposed side surfaces 32 at the maximum thickness T of the brush retaining end 16. Accordingly, as edges 30 are pushed beyond maximum thickness T and the cap 28 is moved to its closed position, the flexed edges relax inwardly to approach and restore to dimension W between the edges. The flexible edges 30 therefore provide an effective but simple means for releasable attachment of the cap 28 to the brush retaining end 16.

Flexible edges 30 therefore permit the cap 28 to be snapped over the brush retaining end 16 of the handle 12 and also permit disengagement of the cap when lifted upwardly to again flex edges 30 outwardly as the edges approach and reach the dimension T. The disengagement of the cap 28 can be facilitated by providing projections 34 extending outwardly from the cap 28 which can easily be lifted or pressed upwardly by a finger of the user.

Thus far, those elements described above are similar to those disclosed in the herein cited U.S. Pat. No. 4,780,923 and it is considered that a further description of the cap structure is unnecessary, as details of the particular cap structures available may be found in the aforementioned patent.

Referring now to FIG. 5, a prior art interproximal brush structure is depicted, the brush 10a comprising a handle having a grip portion and a brush retaining end 16a provided with a transverse hole 18a and longitudinal groove 20a. A brush 24a having a stem 22a is disposed in the handle 12a having a stem 22a and bristle portion 26a. A cap 28a is designed similar in dimension to that of the cap 28, and disposed on the brush retaining end 16a in similar manner to the cap 28 described above.

As previously discussed, the brush 24a has been threaded into the hole 18a and a gap G remains between the bristle portion 26a and the bottom surface of the brush retaining end 16 due to the misconception of the user that the brush has been threaded entirely into the transverse hole 18a. The lack of a stop surface and the employment of clear plastic for the material of the handle 12a all contribute to the user's allowing as much as a quarter inch of unsupported stem length to protrude beyond the bottom surface of the handle 12a.

Referring back to FIGS. 1 through 4, it will be observed that a downwardly extending boss 36 is formed on the lower surface of the brush retaining end 16 having a central opening forming an extension of the hole 18. The boss 36 is in the shape of a frustrum and may be molded during fabrication of the handle 12. The boss 36 is provided with a stop in the form of surface 38 which contacts the more rigid portions of the bristle contained in the bristle portion 26, as best shown in FIGS. 3 and 4.

It will further be observed that a radial convex protuberance 40 is provided in the groove 20 extending laterally across the groove adjacent the transverse hole 18 to aid in bending a portion of the stem 22 extending through the transverse hole and into the groove.

When employing the interproximal brush 10 of the present invention, the user, after opening the cap 28 by pivoting it about the pin 29, inserts the stem 22 of a brush 24 through the opening in the boss 36 and through the hole 18 until the bristle portion 26 contacts the surface 38 of the boss 36. There will be no doubt in the mind of the user that the brush 24 is in place in that the surface 38 provides a positive stop when the bristle portion 26 contacts the surface 38.

Introduction of a new brush into the interproximal brush 10 is now completed when the cap 28 is closed forcing the end of the stem 22 into the groove 20. By providing the protuberance 40, a radial bend is accomplished in the stem 22 which lessens the probability of breakage of the stem during use, at the point of bending. It will be appreciated that with the stem 22 supported as shown in FIG. 3, the angle of the brush in relation to the handle 12 is maintained during usage by virtue of the rigid retention in the boss 36.

While it is apparent that changes and modifications may be made within the spirit and scope of the present invention, it is my intention, however, only to be limited by the scope of the appended claims.

As my invention, I claim.

1. An interproximal brush employing a disposable brush member comprising:

an elongated brush handle having a brush retaining means formed at one end thereof and a grip portion at the opposite end thereof, said brush retaining means comprising opposed side surfaces and a bottom surface of said handle one end, a transverse hole formed in said handle one end and a longitudinal groove in said handle one end arranged for communication with said transverse hole, said bottom surface having a downwardly extending boss formed thereon and disposed with said transverse hole extending through said boss substantially at the centerline thereof;

a brush member having a stem which is inserted through said transverse hole extending through said boss and said handle, and retained in said groove;

a convex radial protuberance extending laterally across said longitudinal groove adjacent said transverse hole to aid in bending a portion of said stem extending through said transverse hole into said groove; and a cap pivotably mounted at the said brush retaining end portion including a section adopted and arranged for overlying said longitudinal groove and the top of said transverse hole.

2. An interproximal brush as set forth in claim 1 wherein said brush retaining means one end is bent upwardly at an angle of from about 5° to about 25° with respect to the longitudinal axis of said handle.

3. An interproximal brush for employing a disposable brush member having an elongated stem, said interproximal brush comprising:

an elongated brush handle having a brush retaining means formed at one end thereof and a grip portion at the opposite end thereof, said brush retaining means comprising opposed side surfaces and a bottom surface of said handle one end, a transverse hole formed in said handle on end and a longitudinal groove arranged for communication with said transverse hole;

a convex radial protuberance extending laterally across said longitudinal groove adjacent said transverse hole to aid in bending a portion of said brush member stem extending through said transverse hole into said groove; and a cap pivotably mounted at the said brush retaining end portion including a section adapted and arranged for overlying said longitudinal groove and the top of said transverse hole.

4. An interproximal brush as set forth in claim 3 wherein said bottom surface of said brush retaining means has a downwardly extending boss formed thereon and disposed with said transverse hole extending through said boss substantially at the centerline thereof.

5. An interproximal brush as set forth in claim 4 wherein said boss is in the form of a frustrum.

6. An interproximal brush employing a disposable brush member comprising:

an elongated brush handle having a brush retaining means formed at one end thereof and a grip portion at the opposite end thereof, said brush retaining means comprising opposed side surfaces and a bottom surface of said one handle end, a transverse hole formed in said handle end and a longitudinal groove disposed in said one end of said handle and arranged for communication with said transverse hole, said bottom surface having a downwardly extending boss formed thereon and disposed with said transverse hole extending through said boss substantially at the centerline thereof;

a cap pivotably mounted at the said brush retaining end portion including a section adopted and arranged for overlying said longitudinal groove and the top of said transverse hole;

a brush member having a stem inserted through said transverse hole extending through said boss and said handle and retained in said groove; and a convex radial protuberance extending laterally across said groove adjacent said transverse hole to aid in bending a portion of said stem extending through said transverse hole into said groove.

7. An interproximal brush as set forth in claim 6 wherein said boss is in the form of a frustrum.

8. An interproximal brush as set forth in claim 7 wherein said brush retaining end portion is bent upwardly at an angle of from about 5° to about 25° with respect to the longitudinal axis of said handle.

* * * * *